(12) United States Patent
Hung et al.

(10) Patent No.: US 7,628,765 B2
(45) Date of Patent: Dec. 8, 2009

(54) INCREASING RETRIEVABLE CELLS FROM A BREAST DUCT

(75) Inventors: David Hung, Redwood City, CA (US); Nathan Wood, Winchendon, MA (US); Robert Sakal, Boston, MA (US)

(73) Assignee: Cytyc Corporation, Marlborough, MA (US)

( * ) Notice: Subject to any disclaimer, the term of this patent is extended or adjusted under 35 U.S.C. 154(b) by 607 days.

(21) Appl. No.: 10/825,752

(22) Filed: Apr. 16, 2004

(65) Prior Publication Data

US 2004/0249317 A1 Dec. 9, 2004

Related U.S. Application Data

(63) Continuation-in-part of application No. 09/827,371, filed on Apr. 6, 2001, now abandoned.

(51) Int. Cl.
*A61H 1/00* (2006.01)

(52) U.S. Cl. ............ 601/15; 600/562

(58) Field of Classification Search ......... 601/15–18; 600/562, 573, 576, 581; 604/28, 30
See application file for complete search history.

(56) References Cited

U.S. PATENT DOCUMENTS

| | | | | | |
|---|---|---|---|---|---|
| 3,765,403 | A | * | 10/1973 | Brenden | 600/448 |
| 4,023,559 | A | * | 5/1977 | Gaskell | 600/572 |
| 4,740,196 | A | * | 4/1988 | Powell | 604/75 |
| 5,012,818 | A | * | 5/1991 | Joishy | 600/567 |
| 5,181,907 | A | * | 1/1993 | Becker | 604/22 |
| 5,255,327 | A | * | 10/1993 | Endo | 381/111 |
| 6,054,314 | A | * | 4/2000 | Kim | 435/325 |
| 6,221,622 | B1 | * | 4/2001 | Love | 435/7.23 |
| 6,391,026 | B1 | * | 5/2002 | Hung et al. | 606/41 |
| 6,413,228 | B1 | * | 7/2002 | Hung et al. | 600/562 |

\* cited by examiner

*Primary Examiner*—Michael A. Brown
(74) *Attorney, Agent, or Firm*—Theodore Allen

(57) ABSTRACT

The invention provides methods that increase retrievable cells from ductal fluid of a patient. Ductal fluid typically contains ductal epithelial cells and other markers that can aid in identifying a breast condition, including breast cancer and precancer.

4 Claims, 1 Drawing Sheet

Shows a Heating Pad and Vibration Device applied to the ductal area of the breast to aid in loosening cells for increased quantities of cell specimen.

Shows a Heating Pad and Vibration Device applied to the ductal area of the breast to aid in loosening cells for increased quantities of cell specimen.

INCREASING RETRIEVABLE CELLS FROM A BREAST DUCT

CROSS-REFERENCES TO RELATED APPLICATIONS

This application is a continuation-in-part of U.S. patent application Ser. No. 09/827,371, filed on Apr. 6, 2001, now abandoned which claims the benefit of each of the following provisional applications under 37 CFR §1.78: 60/114,048, filed on Dec. 28, 1998; 60/134,613, filed on May 18, 1999; 60/143,476, filed on Jul. 12, 1999; 60/143,359, filed on Jul. 12, 1999; and 60/170,997, filed on Dec. 14, 1999. The full disclosures of each these applications are incorporated herein by reference.

BACKGROUND OF THE INVENTION

1. Field of the Invention

The field of this invention is methods and compositions that increases retrievable fluid and cellular material from a breast duct.

2. Description of the Background Art

For several decades significant members of the medical community dedicated to studying breast cancer have believed and shown that the cytological analysis of cells retrieved from nipple discharge from the breast milk ducts can provide valuable information leading to a identifying patients at risk for breast cancer. Indeed Papanicolaou himself contributed to the genesis of such a possibility of a "Pap" smear for breast cancer by analyzing the cells contained in nipple discharge. See Papanicolaou et al, "Exfoliative Cytology of the Human Mammary Gland and Its Value in the Diagnosis of Cancer and Other Diseases of the Breast" Cancer (1958) March/April 377-409. See also Petrakis, "Physiological, biochemical, and cytological aspects of nipple aspirate fluid", *Breast Cancer Research and Treatment* 1986; 8:7-19; Petrakis, "Studies on the epidemiology and natural history of benign breast disease and breast cancer using nipple aspirate fluid" *Cancer Epidemiology, Biomarkers and Prevention* (January/February 1993) 2:3-10; Petrakis, "Nipple Aspirate Fluid in epidemiological studies of breast disease", *Epidemiologic Reviews* (1993) 15:188-195. More recently, markers have also been detected in nipple fluid. See Sauter et al, "Nipple aspirate fluid: a promising non-invasive method to identify cellular markers of breast cancer risk", *British Journal of Cancer* 76(4):494-501 (1997). The detection of CEA in fluids obtained by a nipple blot is described in Imayama et al. (1996) *Cancer* 78: 1229-1234.

Cytological and other analysis of breast ductal fluid that has been made for decades uses nipple aspirate fluid (NAF) collected from the nipple surface upon aspiration of the nipple. Nipple aspiration of the breast yields fluid in the female population in about half the women tested. The fluid retrieved from nipple aspiration has usually several ductal epithelial cells and sometimes as many as 15 or 20 ductal epithelial cells for analysis. Rarely are clumps (groups of about 6 to 10 or more cells) of ductal epithelial cells retrieved by NAF. It is generally believed that NAF pulls fluid from the upper reaches of the ductal network, and usually not more than a cc or so of this fluid is collected at a time. NAF is collected from the nipple surface and cannot consistently be tied to the particular duct from which the aliquot was secreted due to the fact that several ducts can yield fluid and are thus pooled in any given nipple aspiration. Because so few cells are retrieved in NAF, often the fluid, material and/or cell numbers retrieved are insufficient for analysis.

Ductal fluid has been retrieved during galactography, a procedure that is performed upon a condition of spontaneous nipple discharge. Galactography is performed in order to identify the cause of the discharge. In a galactography procedure, a small amount of ductal fluid is collected in an open lumen needle or cannula by syringe-controlled aspiration. This fluid and cell amount is generally about equivalent to NAF yields. Syringe-controlled aspiration with a cannula or lumen in a non-spontaneously discharging duct can result in a collapsed duct that results in no or very little fluid or cell yield. It is presumed that the small amount of fluid retrieved before or after a galactography procedure is retrievable because the duct is full of fluid (and therefore spontaneously discharging). Occult conditions not manifesting spontaneous discharge from the duct do not generally provide an opportunity for intraductal fluid withdrawal.

A non-spontaneously yielding duct can be identified as a high-risk by preliminary nipple aspiration because high-risk ducts tend to yield fluid upon NAF, and these ducts can be accessed with a ductal access tool. The accessed duct can be infused with a biocompatible fluid that mixes with the ductal fluid and cells and other markers. The filled duct can then support aspiration, withdrawal, or otherwise collection of some of this fluid that comprises ductal fluid, ductal epithelial cells, and/or other markers of the breast duct condition.

It would be advantageous to an analysis of breast conditions, particularly assymptomatic occult breast conditions to increase the retrievable fluid and/or cells in one or more ducts in a breast in preparation for a subsequent intraductal access of one or more of these ducts. In addition, increased fluid in the duct provides the opportunity to capture and generate sloughing cells and other markers within the duct.

SUMMARY OF THE INVENTION

The invention is directed to ducts that are not filling and discharging, i.e., ducts that are not spontaneously discharging fluid or material, can be filled intraductally or otherwise treated, e.g., systemically or locally to increase the retrievable fluid in a breast duct, providing the opportunity to access the duct or ducts at a later time and withdraw at least an aliquot of the material (fluid, cells and/or other markers) residing in the artificially filled duct without great risk of ductal collapse and with a return of sufficient material for cytological or other analysis. Without first filling or otherwise increasing the fluid in the duct, intraductal retrieval of the fluid and/or other material is nearly impossible at diagnostically satisfying yields.

One aspect of the invention is a method for preparing for intraductal retrieval of fluid, cells and/or other material from a breast duct of a patient, by administering an agent to the patient that increases retrievable fluid from a breast duct.

Administering can be accomplished by administering an agent intraductally, administering an agent systemically, or administering an agent topically.

An embodiment of the invention includes where an agent is administered intraductally to a breast duct, and the agent can be selected from the group consisting of saline, phosphate buffered saline (PBS), an isotonic solution, a hypotonic solution, a buffered solution, a solution having a pH range of human tissue, blood or sera, a solution having a slightly acid pH, and a solution having a slightly basic pH, a nonabsorbable biocompatable solution.

Another embodiment of the invention includes where the agent is administered systemically the agent can comprise an agent selected from the group consisting of a hormone, oxytocin, prolactin, a breast duct secretion inducing factor, a natural herb or extract from a natural herb, silymarin, a growth factor, a vitamin, a protein, a muscle relaxant, and a small organic molecule.

Another embodiment of the invention includes where the agent is administered intraductally to a breast duct, the agent can be selected from the group consisting of a protein, a colloid, a sugar, a polymer, mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, a synthetic colloid, an antibody, a binding protein, albumin, a hormone, a breast duct secretion inducing factor, a natural herb or extract from a natural herb, silymarin, a surfactant, a growth factor, oxytocin, prolactin, a small organic molecule, a muscle relaxant, a ductal orifice dilator, and an agent that increases fluid secretion from a breast duct epithelium.

The intraductally administered agent can be in a state selected from the group consisting of a non-liquid, a gel, an emulsion, a gas and a semi-solid. The intraductally administered agent can comprise a carbonated fluid comprising super-oxygenated fluid that is colder than room temperature before intraductal administration.

In another aspect of the invention the method can additionally comprise collecting a portion of the increased breast duct fluid from a breast duct. Collecting can comprise accessing a breast duct with a device and withdrawing a portion of the ductal fluid in the reservoir into the device. The method comprising collecting can further comprise analyzing one or more of cells, fluid or other material in the breast duct after the retrievable fluid in the duct has been increased. Analyzing can comprise identifying a marker of a breast condition.

Another aspect of the invention is a method of collecting ductal fluid from a breast duct having artificially increased retrievable ductal fluid comprising accessing a breast duct with a device and withdrawing a portion of the increased ductal fluid into the device. The withdrawn ductal fluid can comprise a marker for identifying a breast condition. The marker can comprises a plurality of ductal epithelial cells.

Another aspect of the invention is a method for increasing a retrievable cell amount in a breast duct comprising inducing cell sloughing within the duct by applying vibration to the duct.

DETAILED DESCRIPTION OF PREFERRED EMBODIMENTS OF THE INVENTION

Figure 1:
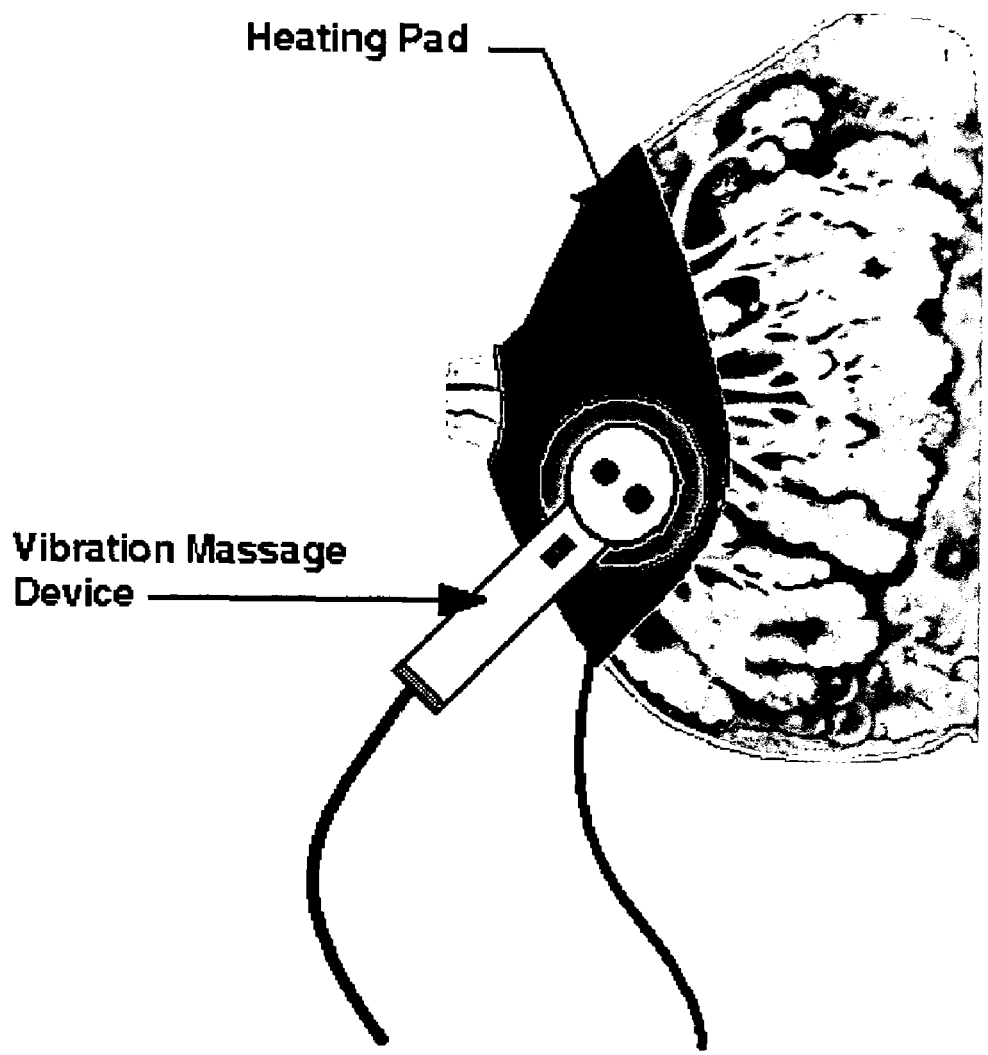
FIG. 1 is an illustration of the application of external vibration and heat to the ductal area of a breast to aid in increasing the amount of retrievable cells in a breast duct by inducing cell sloughing within the duct according to aspects of the present invention.

The following preferred embodiments and examples are offered by way of illustration and not by way of limitation.

The invention provides a method for preparing for intraductal retrieval of fluid, cells and/or other material from a breast duct of a patient. The invention comprises, administering an agent to the patient that increases the retrievable fluid in one or more breast ducts of the patient. Once the retrievable fluid in a breast duct of the patient has been increased, at least a portion of the increased fluid can be analyzed in situ or collected from the breast duct for analysis. An increased fluid reservoir provides the benefit of maximizing the number of cells, markers or other material retrievable from the breast duct.

Successful intraductal retrieval of ductal fluid from a non-spontaneously discharging duct is dependent on increasing the retrievable fluid in the duct so that upon intraductal retrieval of fluid from the duct, the duct will not collapse before at least sufficient fluid (comprising cells, other markers and/or other diagnostically useful material) can be retrieved. Sufficient fluid is generally considered to be that amount of fluid that comprises enough cells and/or other markers to perform an adequate diagnosis of the duct and breast, and will generally be considered to be more fluid volume than retrievable by nipple aspiration. The invention is the discovery that by first artificially increasing the fluid volume or fluid reservoir in a breast duct one can collect sufficient ductal fluid for analysis of the duct and breast. An increased fluid reservoir in the duct can also provide the opportunity for in situ analysis or identification of cells or other markers therein.

Administering the agent to the patient can be accomplished by a mode comprising administering an agent intraductally, administering an agent systemically, or administering an agent topically. Administering an agent intraductally comprises ductal access with a ductal access tool and passing into the duct a sufficient amount of an agent.

The wash fluid that is introduced into the duct can comprise any biocompatible agent or solution. Thus, the wash fluid can comprise, e.g., saline or phosphate-buffered saline. Saline can stay in the duct for a short period of time, and at least a portion of the infused saline can be collected from the duct soon after the saline is infused into the duct. Increasing the retrievable fluid from a breast duct can be accomplished using saline, even though saline does seep out of the duct via the ductal wall or other avenue fairly quickly after it has been infused into the duct. Saline can be used to increase the retrievable fluid in a breast duct provided the saline in the duct is frequently replenished and the procedure to collect the ductal fluid is done soon after or immediately after the duct is filled with the saline. Additionally or alternatively, the wash fluid can comprise an agent or agents or solution that reduces the ability of the fluid or agent to diffuse through the ductal wall or otherwise leave the duct and enter other parts of the body. Accordingly, the wash fluid may comprise a nonabsorbable fluid, an isotonic solution, an osmotic solution, a hypotonic solution or a hypertonic solution. Fluid or agents may be administered to the breast duct in order to facilitate, increase, and/or optimize the amount of material obtained or obtainable from the breast duct during the procedure. Agents or solutions that may comprise the infused wash fluid can include, e.g., protein, colloid, sugar, polymer, mannitol, sorbitol, glucose, glycerol, sucrose, raffinose, fructose, lactulose, sodium chloride, polyethyleneglycol (PEG), maltodextrin, dextran (e.g., dextran 70), hydroxyethyl starch, fluid gelatin, albumin, a synthetic colloid, an antibody or part of an antibody, or a binding protein.

Administering fluid to the ductal lumen for the purpose of increasing the retrievable fluid in a breast duct and also later collecting that fluid mixed with the fluid from the duct is complicated by the fact that absorbable wash fluids are partly absorbed into the breast tissue from the ductal walls. Thus, the fluid retrieved is less than that infused, even considering that it includes the ductal fluid that was residing in the duct. Administering an agent in the wash fluid that is capable of increasing or maintaining the fluid volume in the duct is a great advantage to the process. Thus, the invention provides administering a nonabsorbable fluid or a fluid that actually draws fluid to it, e.g., an oncotic or osmotic fluid in the process of collecting fluid from the duct. Administering the nonabsorbable fluid has the advantage also of providing the practitioner with a way to monitor or standardize the ductal fluid and cellular return in any given volume of fluid infused and retrieved. For example, 10 ml of the nonabsorbable fluid is administered to the duct, and 9.5 ml of that fluid is collected. One hundred epithelial clusters may be contained in the fluid collected. This information can be noted and compared with future procedures on that same duct. The advantage of using a nonabsorbable fluid is that the ductal fluid yield may be increased with the retrieval of most or all of the infused fluid, and the practitioner will be able to keep track of the amount infused versus the amount collected. A nonabsorbable fluid can be used in order to provide standardization to the process so that the amount infused can be correlated with the amount collected. Since the fluid cannot be absorbed by the duct it is possible to collect all or most of the fluid that is infused.

The agent can be an agent capable increasing the amount of retrievable or collectable fluid in the ductal lumen. Thus the agent can be a nonabsorbable agent or fluid or an oncotic agent and/or an osmotic agent or a combination of two or all three. Oncotic and osmotic agents are agents that retain fluid around them or draw fluid to them. The agent can be soluble, e.g., soluble in a suitable solvent, including, e.g., water, buffered water, or a saline solution. Preferably the solvent is biologically compatible with mammals. Suitable solvents will be those that both effectively dissolve the agent and are not toxic to a mammal.

The agent can be a molecule including, e.g., a protein, colloid, sugar, or polymer. The agent can be mannitol, sorbitol, glucose, glycerol, sucrose, raffinose, fructose, lactulose, sodium chloride, albumin, polyethyleneglycol (PEG), maltodextrin, dextran (e.g. dextran 70), hydroxyethyl starch, fluid gelatin, or a synthetic colloid. Agents including e.g. mannitol, sorbitol, PEG, glycerol is described in THE MERCK INDEX, $12^{th}$ ed. 1996, Whitehouse Station, N.J. Others, including maltodextrin, dextran and others are available from Aldrich Chemical Co. in Milwaukee, Wis. or Sigma Chemical Co. in St. Louis, Mo. The molecular weight of a suitable oncotic agent can be determined as optimally within the range of the molecular weights of suitable oncotic agents available. Also the agent can be a mixture of osmotic and/or oncotic agents. The oncotic agent and/or osmotic agent can comprise a mixture of any two or more osmotic and/or oncotic agents, e.g., mannitol, sorbitol, glucose, glycerol, sucrose, raffinose, fructose, lactulose, sodium chloride, albumin, polyethyleneglycol (PEG), maltodextrin, dextran (e.g. dextran 70), hydroxyethyl starch, fluid gelatin, an antibody or a synthetic colloid.

Where the agent is a protein, the protein can be a binding protein or an antibody. The binding protein can be albumin. The antibody can be capable of binding an epitope found in a breast duct, e.g., an epithelial cell surface marker or cancer cell marker, etc. Where the agent is a protein, the protein is of a molecular weight in the neighborhood of albumin or higher, so that it is capable of acting as an oncotic agent in the lumen of the milk duct. Suitable antibodies are commercially available. The agent can be an agent not capable of freely diffusing into or beyond the cells that line the milk ducts of the breast. The agent can also be an agent not capable of absorption into the cells within the duct. For example, the agent can have a molecular weight large enough to make absorption or diffusion into the breast duct lining, cells or interstitial space beyond the lining improbable.

Whether an agent is capable of increasing or at least maintaining the amount of collectable fluid (with relation to the amount of fluid infused) in the ductal lumen can be determined by routine tests to determine whether collectable fluid in the duct is increased upon administration of an agent as compared to administration of a control isotonic solution to a neighboring control duct. Likewise the best volume and concentration of the agent can be determined by a comparison of the amount of collectable fluid yielded with a change in a variable such as a volume or concentration of agent administered. The agents including nonabsorbable fluid and/or oncotic and/or osmotic agents to be tested can be delivered to the duct of a human, rat, rabbit, pig or other appropriate mammal, and the ductal fluid can be collected. Where the fluid yield is greater than control fluid collected from a neighboring duct (after injection of a control solution, preferably of equal volume as the tested solution), that agent is suitable for use in the method. In the case where the practitioner seeks to increase the amount of fluid collected from the amount infused, the fluid yield from the duct administered with the agent being tested can be several fold that of the control fluid yield. Where the goal is merely to provide for a collection fluid amount that is close to the amount infused, the parameters for success are that the amount of fluid collected from the duct after infusion of a set aliquot of fluid is closer to the amount infused that would have been possible if the infusion fluid had been an absorbable fluid such as saline. Such a comparison can be tested by doing a control infusion and collection in a duct using, e.g., saline and then repeating the procedure in the same duct using a nonabsorbable fluid, e.g., a PEG containing fluid or the like.

The appropriate concentration and volume of oncotic agent and/or osmotic agent in solution injected into a duct can be determined by routine experimentation including cannulation or catheterization of mammalian nipples (e.g. rat, rabbit, pig or human nipples) to determine at which concentration and volume the agent in solution yields the most volume of fluid collectable from the duct as compared to the fluid collectable from a control duct. Experiments can be designed for testing a variety of oncotic and/or osmotic agents, concentrations, volumes, and mixtures of agents in all varieties of mammals having breast ducts.

Thus an agent administered intraductally for the purpose of increasing a ductal fluid reservoir can comprise, e.g., a protein, a colloid, a sugar, a polymer, mannitol, sorbitol, glucose, glycerol, sucrose, raffinose, fructose, lactulose, sodium chloride, polyethyleneglycol (PEG), maltodextrin, dextran (e.g., dextran 70), hydroxyethyl starch, fluid gelatin, a synthetic colloid, an antibody, a binding protein, or albumin. The agent administered intraductally can additionally comprise, e.g., saline, phosphate buffered saline (PBS), an isotonic solution, a hypotonic solution, a buffered solution, a solution having a pH range of human tissue, blood or sera, a solution having a slightly acid pH, and a solution having a slightly basic pH, a nonabsorbable biocompatable solution. The molecular weight of a suitable oncotic agent can be determined as optimally within the range of the molecular weights of suitable oncotic agents available. The intraductally administered agent can comprise a molecule that acts on the patient so that the breast duct to increases its fluid reservoir. Thus the intraductally administered agent can comprise, e.g., a hormone, a breast duct secretion inducing factor, a natural herb or extract from a natural herb, e.g., silymarin, a growth factor, oxytocin or prolactin, a small organic molecule, a muscle relaxant, a ductal orifice dilator, and an agent that increases fluid secretion from a breast duct epithelium.

The fluid can further contain other agents that may aid in the retrieval of fluid or cells or both from the duct or may serve some other useful purpose in the procedure. For example, the fluid may include or be preceded by or followed by such other agents that may aid in the retrieval of fluid or cells or both from the duct, or may serve some other useful purpose in the procedure. Such other agents can be, for example, an oncotic and/or osmotic agent capable of increasing the amount of collectable fluid in the ductal lumen, or a detergent that can help wash out more cells, or an agent that may help detach more cells from the duct wall into the ductal lumen (e.g., trypsin, collagenase, or EDTA). The agent can be an oncotic agent and/or an osmotic agent or both. Oncotic and osmotic agents are agents that retain fluid around them or draw fluid to them. The agent can be soluble, e.g., soluble in a suitable solvent, including, e.g., water, buffered water, or a saline solution. Preferably the solvent is biologically compatible with mammals. Suitable solvents will be those that both effectively dissolve the agent and are not toxic to a mammal. The agent can be liquid, gas, solid or semi-solid, for example. The agent may also change its state upon administration, for example, a super-cooled gas can be liquefied and administered to the duct as a cool liquid, which becomes gaseous upon contact with the duct environment. Saline can be administered to the duct but after a period of time, saline may be absorbed by the duct. Molecules in solution which draw fluid to them, e.g., oncotic or osmotic agents can increase a ductal fluid reservoir, and/or increase the retrievable fluid in a breast duct. The agent or agents to increase the retrievable ductal fluid can also comprise an agent in a state including, e.g., a non-liquid, a gel, an emulsion, a gas, or a semi-solid.

The fluid will generally be biocompatible and nontoxic to the patient. The fluid can further comprise additives, e.g., gas, particles, emulsions or other fluids. These additives to the fluid may have various purposes, however, during a procedure, the main purpose will generally be to increase a recovery of fluid and/or cellular material, and/or molecular species from the ducts. Thus, such gas may provide a cleansing action on the ductal walls for example, encouraging ductal epithelial cells located, e.g., in a lesion in the duct to shed and be retrievable during the ductal access procedure. Similarly, particle additives may serve to encourage fluids, cellular material and/or molecular species to follow the particles in the flow of fluid through the ducts and be retrieved in the ductal access procedure. Such additives as detergents, e.g., agents tending to form micelles for collecting ductal contents including cells and molecular species may provide additional yields of cells, molecular species and fluids in a lavage procedure. The gas can be ambient air or a related product, and the fluid can comprise the air mixed in with the fluid for delivery into the duct. The presence of air or other gas may serve to increase the retrieval of cells and fluid as compared to a procedure conducted using fluid alone. The air can be bubbled into the fluid, or introduced into the fluid mixture by other standard means. The air may also be mixed into the fluid as the fluid is delivered into the duct, e.g. where the infusion port allows for delivery of both air and fluid into the inflow lumens where the two mix and both are delivered to the accessed ducts.

An agent can be administered systemically to the patient in order to increase a ductal fluid reservoir. For example, the systemically administered agent can comprise, e.g., oral, parenteral, subcutanous, intramuscular, intravenous, suppository, or other administration procedure that is systemically received by the body, albeit the agent or agents affecting the breast ducts by promoting an increase in their ductal fluid reservoir. The agent can be, e.g., a hormone, e.g., oxytocin, or prolactin, a breast duct secretion inducing factor, a natural herb or extract from a natural herb, e.g., silymarin, a growth factor, a surfactant, a vitamin, a protein, a muscle relaxant, or a small organic molecule.

Topically administered agents can be placed in contact with the nipple surface and a ductal orifice in order to promote an increased fluid reservoir in the duct, or easier access and retrieval from the duct of any fluid, materials or cells therein.

After a fluid reservoir has been increased a portion of the increased fluid reservoir can be collected. Or, alternatively, the material, fluid, markers or cells in the duct having the increased reservoir can be analyzed or identified in situ. Analyzing the collected material or analyzing the material in situ can comprise identifying a marker of a breast condition. Collecting ductal fluid from a breast duct having artificially increased the retrievable fluid in the breast duct can comprise accessing a breast duct with a device and withdrawing a portion of the ductal fluid in the reservoir into the device. The withdrawn ductal fluid can comprises a marker for identifying a breast condition. The marker can comprise a plurality of ductal epithelial cells.

A method of the invention can also comprise increasing a retrievable cell amount in a breast duct by inducing cell sloughing within the duct by applying vibration or other motion or movement that induces cell sloughing to the duct. Vibration may be applied externally to the breast or internally through a device inserted directly into the breast duct (see FIG. 1). Vibration devices include, but are not limited to, ultrasound (including ultrasound devices used in medical procedures, for example, extracoporeal shock wave lithotripsy, ultrasound enhanced thrombolysis, acoustic hemostasis), and other sonic devices. The application of a method of vibration to increasing a retrievable cell amount in a breast duct may also be combined with other therapeutic treatments such as heat or massage. When applying heat, vibration, or ultrasound directly to the breast, the use of a medium such as water, gel, or other liquids or semi-solids can be used to prevent damage to the skin or surrounding tissue. These additional techniques may assist in the retrieval of ductal fluid and/or cellular material by relaxing ductal sphincters and increasing blood flow to the breast. Increasing a retrievable cell amount in a breast duct can also comprise administering surfactant intraductally to the breast duct. The surfactant can act to increase the amount of cells in the ductal fluid and thus increase the cell population available for analysis.

The cells collected can comprise ductal epithelial cells; the ductal fluid collected can comprise molecular and cellular material. Analysis of the ductal epithelial cells and/or the molecular and cellular material in the ductal fluid can proceed using available methods for analysis of these collected materials; the collected cells and fluid and fluid components can be analyzed, e.g., as described or suggested herein. The fluid including the ductal cells can be analyzed for diagnostic purposes. Conditions in a breast milk duct that are desirable to diagnose include a cancer or precancer condition. The precancer condition can include atypical ductal hyperplasia (ADH) or low grade ductal carcinoma in situ (LG-DCIS). The diagnostic agent may also have the ability to identify other breast related conditions, including, e.g., fibrotic, cystic or conditions relating to lactation. Diagnostic agents can be mixed with the ductal fluid (either in a ductal access procedure, or after the fluid is collected).

For example, any of the cells of the duct can be analyzed for morphological abnormalities in cell components, including, e.g., morphological abnormalities of the nucleus, cytoplasm, Golgi apparatus or other parts of a cell. The cells can be analyzed for whether they do or don't aggregate (e.g., in clumps) or by making comparisons of the ductal epithelial cells with other cell types retrieved in the ductal fluid (e.g., macrophages, lymphocytes, foam cells and other possible components of ductal fluid). The ductal epithelial cells can be analyzed, e.g., for their molecular contents or the morphology of the ductal epithelial cells, including, e.g., protein markers, nucleic acid markers, biochemical markers in the cells or on the cell surfaces or for any evidence of neoplasia. Analysis of cell contents may serve to establish similar staging as established by morphology, capturing generally a progression of a precancerous or cancerous condition in the cells.

In addition, fluid collected from the milk ducts, can include constituents of biological fluids, e.g., those typically found in breast duct fluid, e.g., water, cells, cellular markers, molecular markers, nucleic acids, proteins, cellular debris, salts, or organic molecules. These constituents can be analyzed by any appropriate method depending on the practitioner's purposes in obtaining the fluid.

Standard assay procedures for identifying the markers can be used. Collected samples can be analyzed for the presence of soluble factors or other components that might indicate the presence of cancerous or precancerous ductal epithelial cells in the duct. The epithelial cells retrieved from the breast duct can be analyzed for protein markers, nucleic acid markers, chromosomal abnormalities, or other characteristic changes that would signal the presence of cancerous or precancerous cells. In addition, other cells found in the duct can also be analyzed, e.g., for an increase or decrease in these cells as compared to normal ductal fluid, or for qualities of these cells themselves. Thus, the condition of the breast duct can be analyzed, e.g., for soluble protein content or presence of other ductal fluid components, including also secreted products of ductal epithelial cells) or the ductal epithelial cells themselves can be analyzed, for example, for cell morphology, for protein markers, for nucleic acid markers, and for biochemical markers.

Cytological assays that can be performed on the cells retrieved from a duct or from nipple aspirate can include, e.g., assays described in King et al, *J. Nat'l Cancer Inst* (1983) 71:1115-21, Wrensch et al. (1992) *Am. J. Epidem.* 135: 130-141, Papanicolaou et al, (1958) *Cancer,* 11:377-409 and Goodson W H & King E B, Chapter 4: *Discharges and Secretions of the Nipple*, THE BREAST: COMPREHENSIVE MANAGEMENT OF BENIGN AND MALIGNANT DISEASES (1998)$2^{nd}$ Ed. vol 2, Bland & Kirby eds. W.B. Saunders Co, Philadelphia, Pa. pp. 51-74. For example, as described in Goodson and King (page 60) atypical hyperplasia presents as having cellular abnormalities, increased coarseness of the chromatin, and tendency for more single cells as well as groups of cells. With regard to carcinoma in situ, Papanicolaou et al, described cellular abnormalities, e.g. nuclear abnormalities diagnosed by cytology of fluid from nipple secretions containing ductal cells. The cytology of abnormal cells can also be conducted as described in Sartorius et al (1977) *J. Natl Cancer Inst* 59: 1073-1080. and King et al, (1983) *JNCI* 71(6) 1115-1121. Atypia and carcinoma in situ are widely characterized pathologically, as described in Page et al, (1998) *Mod Pathol* 11(2): 120-8. The ductal fluid can be analyzed by cytological techniques by placing some of the fluid on a slide with a standard cytological stain using a light microscope. The cells can be studied for atypical growth patterns in individual cells and clusters of cells using published methods, including Mouriquand J, (1993) S Karger Pub, "Diagnosis of Non-Palpable Breast Lesions: Ultrasonographically Controlled Fine-Needle Aspiration: Diagnostic and Prognostic Implications of Cytology" (ISBN 3805557477); Kline T S and I K, Pub Igaku-Shoin Medical "Breast: Guides to Clinical Aspiration Biopsy" (LSBN 0896401596; Masood, *American Society of Clinical Pathology*: Nov. 199S, "Cytopathology of the Breast" ISBN 0891893806; and Feldman PS, *American Society of Clinical Pathology*, November 1984, "Fine Needle Aspiration Cytology and Its Clinical Applications: Breast and Lung" ISBN 0891891846.

Other references that discuss cytological analysis and which give guidance to an analysis of ductal epithelial cells derived from ductal fluid include Silverman et al, (Can FNA biopsy separate atypical hyperplasia, carcinoma in situ, and invasive carcinoma of the breast?: Cytomorphologic criteria and limitations in diagnosis, Diagnostic Cytopathology) 9(6): 713-28, 1993; Masood et al, (Immunohistochemical differentiation of atypical hyperplasia vs. carcinoma in situ of the breast) *Cancer Detection & Prevention.* 16(4):225-35, 1992; Masood et al, (Cytologic differentiation between proliferative and nonproliferative breast disease in mammographically guided fine-needle aspirates) *Diagnostic Cytopathology.* 7(6):581-90, 1991; Masood S., (Occult breast lesions and aspiration biopsy: a new challenge) Diagnostic Cytopathology. 9(6):613-4, 1993; Masood S., (Prognostic factors in breast cancer: use of cytologic preparations) *Diagnostic Cytopathology.* 13(5):388-95, 1995; Novak and Masood, (Nuclear grooves in fine-needle aspiration biopsies of breast lesions: do they have any significance?) *Diagnostic Cytopathology.* 18(5):333-7, 1998; Sidawy et al, (Interobserver variability in the classification of proliferative breast lesions by fine-needle aspiration: results of the Papanicolaou Society of Cytopathology Study) *Diagnostic Cytopathology.* 18(2):150-65, 1998; Masood et al, (Automation in cytology: a survey conducted by the New Technology Task Force, Papanicolaou Society of Cytopathology)*Diagnostic Cytopathology.* 18(1): 47-55, 1998; and Frykberg and Masood Copeland E M 3d. Bland K I., (Ductal carcinoma in situ of the breast) *Surgery, Gynecology & Obstetrics* 177(4):425-40, 1993.

The invention includes a kit for increasing the amount of fluid retrievable from a milk duct of a breast comprising an agent for intraductal administration, a medical tool for delivering the agent intraductally to the patient, and instructions for use. The agent is an agent that can increase the retrievable ductal fluid and material in a breast duct. The medical tool can be any tool that provides intraductal delivery of such agent. The instructions can direct a protocol for administration including how to administer the agent, how much time to wait before collecting the fluid, how to collect the fluid, and how to analyze or prepare for analysis the collected fluid.

EXAMPLES

Mannitol Solution Introduced into Breast Ducts of Live Rabbit Results in Increased Ductal Fluid Collection The objective of these experiments was to test the effects of the introduction of a solution containing mannitol on the secretion of fluid from the breast ducts of live rabbits. New Zealand rabbit #3242, female, from Kraelik Farm in CA weighing 4.1 kg was used. The rabbit was anesthetized by injection of 200 mg of ketamine and 40 mg of Zylazine. A second injection of 100 mg of ketamine and 20 mg of xylazine was made 2 hours later to maintain the rabbit in a deep plane of anesthesia. The thorax and abdomen of the rabbit was shaved to expose the breasts and nipples.

A single lumen blue color catheter (O.D. 0.23" ID 0.017; O.D. at the tip 0.011"-0.012") was inserted into a duct in each nipple. Three nipples were tested, and 2 ducts per nipple were accessed with a catheter. The nipples were identified A, B, and C.

A duct on nipple A was injected with 0.20 ml of a 12.5% solution of D-Mannitol in $H_2O$ (available from Sigma Chemicals, St. Louis, Mo. cat# M-9546 lot 6710402: $C_6H_{14}O_6$ FW 182.2) with a single catheter. The control duct on nipple A was injected with 0.20 ml of phosphate buffered saline (PBS).

A microfuge tube was attached to the end of each catheter to collect out flow liquid. Ten minutes later 0.2 ml of a 12.5% solution of D-Mannitol in H$_2$O was injected into the first duct and the second duct was injected with 0.20 ml of phosphate buffered saline, for a total volume injected in each duct of 0.40 ml.

A duct on nipple B was injected with 0.5 ml of a 12.5% solution of D-Mannitol in H$_2$O with a single catheter. The control duct on nipple B was injected with 0.50 ml of phosphate buffered saline (PBS). A microfuge tube was attached to the end of each catheter to collect out-flow liquid.

A duct on nipple C was injected with 0.7 ml of a 12.5% solution of D-Mannitol in H$_2$O with a single catheter. The control duct on nipple C was injected with 0.70 ml of phosphate buffered saline (PBS). A microfuge tube was attached to the end of each catheter to collect out flow liquid.

About an hour after the fluid containing mannitol or PBS was injected into the ducts via the catheters, the microfuge tubes were checked for whether any fluid was returned. The results are summarized in the following Table III:

TABLE III

| nipple | duct | solution | recovery | notes |
| --- | --- | --- | --- | --- |
| A | A1 | 0.4 ml mannitol 12.5% | 310 ul liquid | fluid was a milky color |
| A | A2 | 0.4 ml PBS | none | — |
| B | B1 | 0.5 ml mannitol 12.5% | 490 ul liquid | fluid was a milky color |
| B | B2 | 0.5 ml PBS | 240 ul liquid | fluid was a milky color |
| C | C1 | 0.7 ml mannitol 12.5% | 280 ul liquid | fluid was a milky color |
| C | C2 | 0.7 ml PBS | none | — |

Davidson green dye (1 ul) was added to each microfuge tube containing fluid for the purpose of taking a picture. The rabbit was euthanized by IV injection of supersaturated KCl. PBS (1.5 ul) was added to each collection. The cells were spun onto Shandon coated slide using megafunnel and cytospin-3 machine (Shandon, Inc. located in Pittsburgh, Pa.) at a speed of 1500/per minute for 15 minutes. The cells were fixed on the slide in 95% ethanol for 10 minutes. The cells were stained using Hematoxylin and Eosin (HE) method of cytology of collected fluid. The results of the cellular analysis are in Table IV:

TABLE IV

| Nipple A/ duct A1 | Nipple B/ duct B1 | Nipple B/ duct B2 | Nipple C/ duct C1 |
| --- | --- | --- | --- |
| A few ductal cell clusters and scattered histocytes and apocrine metaplastic cells | A few ductal cell clusters and scattered histocytes and apocrine metaplastic cells | A few ductal cell clusters and scattered histocytes and apocrine metaplastic cells | A few ductal cell clusters and scattered histocytes and apocrine metaplastic cells |

The observations made from this experiment are that fluid can be collected from three out of three ducts injected with mannitol solution; that fluid could be collected from 1 out of 3 ducts injected with PBS solution, and with approximately 50% less volume in the ducts where fluid was collected. There were cells detected from the fluid collected from each duct. The cell morphology looked similar between the mannitol and the PBS injected ducts.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for increasing a retrievable cell amount in a breast duct comprising the steps of:
    applying vibration internally to a breast duct sufficient to induce cell sloughing within said breast duct and;
    collecting said sloughed cells from said breast duct;
    wherein applying vibration to said breast duct increases the retrievable amount of cells collected from said breast duct.

2. A method as in claim 1, wherein said vibration is produced by ultrasound.

3. A method as in claim 1, wherein said vibration is combined with heat and/or massage.

4. A method as in claim 1, wherein said retrievable cell amount is collected through ductal lavage.

* * * * *